(12) United States Patent
Buchold et al.

(10) Patent No.: US 7,598,410 B2
(45) Date of Patent: Oct. 6, 2009

(54) METHOD FOR THE PRODUCTION OF ORGANIC CARBONATES

(75) Inventors: Henning Buchold, Hanau (DE); Jürgen Eberhardt, Rodgau (DE); Ulrich Wagner, Biendorf (DE); Hans-Jörg Wölk, Rosenheim (DE)

(73) Assignee: Lurgi GmbH, Frankfurt am Main (DE)

( * ) Notice: Subject to any disclaimer, the term of this patent is extended or adjusted under 35 U.S.C. 154(b) by 468 days.

(21) Appl. No.: 10/571,479

(22) PCT Filed: Jul. 16, 2004

(86) PCT No.: PCT/EP2004/007913

§ 371 (c)(1),
(2), (4) Date: Dec. 28, 2006

(87) PCT Pub. No.: WO2005/028415

PCT Pub. Date: Mar. 31, 2005

(65) Prior Publication Data

US 2007/0203322 A1 Aug. 30, 2007

(30) Foreign Application Priority Data

Sep. 11, 2003 (DE) .............................. 103 41 951

(51) Int. Cl.
*C07C 69/96* (2006.01)
(52) U.S. Cl. ...................................... 558/260
(58) Field of Classification Search ............... None
See application file for complete search history.

(56) References Cited

U.S. PATENT DOCUMENTS 4,436,668 A  3/1984  Harder et al. ............... 260/463
5,489,702 A  2/1996  Doya et al. .................. 558/277
6,031,122 A  2/2000  Mizukani et al. ............ 558/277

FOREIGN PATENT DOCUMENTS

EP  0478073  4/1992

*Primary Examiner*—Kamal A Saeed
(74) *Attorney, Agent, or Firm*—Andrew Wilford

(57) ABSTRACT

The invention relates to a method for the production of monomer organic carbonates from a mixture of organic carbonates and carbamates which are obtained by reacting urea, substituted urea, a salt or ester of carbamide acid or one of the N-substituted derivatives thereof with a polyalkylene glycol, polyester-polyol or a polyether-polyol of general formula (I), wherein R represents a linear or branched alkylene group having 2-12 carbon atoms and n represents a number between 2 and 20, or with a completely or partially hydrolysed polyvinyl alcohol of general formula (II), wherein R' represents an alkyl group, an aryl group or an acyl group having 1-12 carbon atoms, p and q represent a number between 120, or with mixtures of said compounds in the presence of a catalyst facilitating the separation of ammonia and the ammonia becomes free or the amine is removed from the reaction mixture by means of a strip gas, whereby said mixture is reacted with an alcohol or a phenol whereby monomer carbonates are formed and polymer polyalcohols of formulae (I) or (II) are reformed.

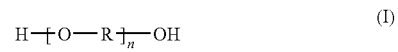

5 Claims, No Drawings

METHOD FOR THE PRODUCTION OF ORGANIC CARBONATES

CROSS REFERENCE TO RELATED APPLICATIONS

This application is the US national phase of PCT application PCT/EP2004/007913 filed 16 Jul. 2004 with a claim to the priority of German patent application 10341951.9 itself filed 11 Sep. 2003.

The subject of the invention is a method for the manufacture of organic carbonates from a mixture of polyalcohols and their carbonates and carbamates.

Organic carbonates, such as dimethyl carbonate and diphenyl carbonate are of great significance as intermediates for a multiplicity of syntheses in the chemical industry.

Thus dimethyl carbonate is a starting material for aromatic polycarbonates. Dimethyl carbonate is transesterified with phenol to the diphenyl carbonate and converted in a melt polymerization with bisphenol to the aromatic polycarbonate. (Daniele Delledonne; Franco Rivetti; Ugo Romano: "Developments in the Production and Application of Dimethyl Carbonate" Applied Catalysis A: General 221 (2001) 241-251). Dimethyl carbonate can be employed for the improvement of the octane number of gasoline and substituted for environmentally troublesome additives like MTBE (Michael A. Pacheco; Christopher L. Marshall: "Review of Dimethyl Carbonate (DMC) Manufacture and its Characteristics as a Fuel Additive" Energy and Fuels 11 (1997) 2-29. In this connection above all the easy biodegradability, the non-toxicity and the good applicability as a gasoline additive is to be mentioned. Dimethyl carbonate has a range of applications in chemical synthesis. At temperatures at or under the boiling temperature of 90° C. dimethyl carbonate can be used as a methoxylating agent. At higher temperatures around 160° C. dimethyl carbonate can be employed as a methylating agent (Pietro Tundi; Maurizio Selva: "The Chemistry of Dimethyl Carbonate" Acc. Chem. Res. 35 (2002) 706-716).

Up to about 1980 the method used for the manufacture of dimethyl carbonate was the alcoholysis of phosgene with methanol (U.S. Pat. No. 2,379,740, Pittsburgh Plate Glass Company 1941) or (Kirk-Othmer, Encyclopedia of Chemical Technology, $3^{rd}$ Edition, Volume 4, 758). The toxicity of phosgene and formation of corrosive hydrogen chloride of course militate against an environmentally conscious commercial use on a large scale.

To date the mainly utilized process is the conversion of methanol with carbon monoxide and oxygen in contact with copper chloride, described in U.S. Pat. No. 5,210,269 by Enichem (1993). This oxidative carbonylation involves running over copper methoxy chloride and a subsequent reaction with carbon monoxide to dimethyl carbonate. The main problem of this process is the deactivation of the catalyst by water. The deactivated catalyst must be expensively regenerated or the water content in the reactor be held low.

A variant of the oxidative carbonylation is a two-stage reaction over methyl nitrite. In a pre-reactor methyl nitrite is synthesized from methanol, nitric oxide and oxygen, wherein water is formed as a byproduct. After removal of the water gaseous methyl nitrite is converted with CO to dimethyl carbonate in a solid bed reactor on a palladium chloride catalyst; The NO formed is fed into this circuit. This method has the disadvantage that the operation with corrosive nitric oxide is dangerous.

Another possibility for the manufacture of dimethyl carbonate is the transesterification of a cyclic carbonate with methanol. Methods with ethylene or propylene carbonate as starting material are known (U.S. Pat. No. 4,734,518 Texaco 1988; U.S. Pat. No. 4,691,041 Texaco 1987). Starting from the cyclic carbonate the dimethyl carbonate can be synthesized and simultaneously in each case one mole of the corresponding diol. The alkylene carbonates can be simply prepared. The disadvantage of this method is the co-production of diols with the manufacture of dimethyl carbonate.

The direct alcoholysis of urea with methanol is another possibility fro the manufacture of dimethyl carbonate. The synthesis goes in two steps via the carbamic acid methylester to the dimethyl carbonate. The reaction rate is strongly inhibited through the ammonia that is formed. For the improved synthesis therefore chemical and physical methods were proposed to remove the ammonia which is formed.

Also a precipitation of the ammonia formed by means of $BF_3$ was successfully performed (U.S. Pat. No. 2,834,799, 1958), but is uneconomical in view of the higher salt loads arising.

The removal of ammonia (U.S. Pat. No. 4,436,668; BASF 1984) by addition of inert gas in a second stage furnished up to now only unsatisfactory conversions and selectivities. For improvement of the process, a second stage was employed with a reacting catalyst diakyl isocyanatealkoxy tin (U.S. Pat. No. 5,565,603; Exxon 1996; U.S. Pat. No. 5,561,094; Exxon 1996), which is prepared in situ through methanol. As a disadvantage the preparation and processing of the reacting catalyst is to be mentioned.

An alternative to the direct synthesis is the operation of a cyclic carbonate (U.S. Pat. No. 5,489,702 Mitsubishi Gas Chemical 1996; U.S. Pat. No. 5,349,077; Mitsubishi Gas Chemical 1994). Here in a first step a diol is reacted with urea and a cyclic alkylene carbonate with 5 or 6 ring atoms is synthesized. In the second process step the alkylene carbonate is transesterified with methanol. The diol can subsequently be fed into the circuit.

The intermediate products produced in the alcoholysis must subsequently be transesterified with methanol, in order to obtain dimethyl carbonate as product. The transesterification is a catalyzed reaction. As heterogeneous catalysts basic alkali and alkaline earth metals or oxides are employed. Examples of alkaline or alkaline earth metals in zeolites are given in U.S. Pat. No. 6,365,787 by Exxon. Examples of metal oxides are named in U.S. Pat. No. 6,207,850 Mobil Oil. Methods for the transesterification of ethylene and propylene carbonates with alcohols in counter current solid bed tube reactors with homogeneous or heterogeneous catalysts (U.S. Pat. No. 5,231,212; Bayer 1993; U.S. Pat. No. 5,359,188; Bayer 1994) as well as a method patent for the synthesis by means of epoxides with subsequent transesterification on bifunctional catalysts (U.S. Pat. No. 5,218,135; Bayer 1993) are likewise already known. The transesterification of cyclic carbonates with alcohols in a reactive distillation is described (U.S. Pat. No. 6,346,638; Asahi Kasai Kabushiki Kaisha 2002). A reactive extraction with hydrocarbons or gasoline as phases for the absorption of dimethyl carbonate and a polar phase of alkylene carbonate for absorption of the alcohols is known from U.S. Pat. No. 5,489,703.

Only a few of these are in principle promising possible synthesis routes for a engineering and economical realization. For the large quantities of dimethyl carbonate required only those methods come into consideration which also have available the necessary inexpensive raw materials in sufficient quantities. In recent years therefore the manufacture of organic carbonates preferably dimethyl carbonate, on the basis of urea and methanol, has been strenuously worked on to implement on an engineering scale. Despite numerous developments the methods described up to now partly possess significant disadvantages, so that an elegant commercial route for the production of organic carbonates, such as DMC is still lacking.

As disadvantageous the methods described up to now show:

The reaction of urea with methanol proceeds via the intermediate stage of carbamates.

During the reaction ammonia is split off, which must be removed.

Because of insufficient ammonia separation the reaction proceeds with only small degrees of conversion.

Ammonia can in principle be removed from the reaction mixture via different methods, however in the methods known from the state of the art, hereby a solid material to be disposed of forms or a large part of the methanol employed is also removed.

Large amounts of methanol must be utilized in the circuit.

A method developed for DMC can not automatically be extended from the synthesis of other carbonates.

In order to overcome these disadvantages a new intermediate product and a synthesis was described in the simultaneously filed patent application (internal reference L 1 P 22), which has such a high boiling point that it is not also removed in the necessary expulsion of ammonia by means of stripping.

This intermediate product is a mixture of different polyalcohols and their carbonates and carbamates and has the special advantage that it can then fulfill a function as auxiliary material for the manufacture of organic carbonates when it is not in pure form, but is present as a mixture. By using this mixture as well as the solubility for the urea also as also the boiling behavior the requirements of ammonia removal can be adjusted correspondingly. The use of this intermediate product for the manufacture of organic carbonates is the subject of the present application.

The method for the manufacture of organic carbonates in accordance with the invention comprises therein that a mixture of polyalcohols and their organic carbonates and carbamates, which through reaction of urea, a substituted urea, a salt or ester of carbamic acid or one of its N-substituted derivatives (alkyl, aryl groups like methyl, ethyl, phenyl, benzyl) with polymeric multifunctional alcohols like polyalkyleneglycols, polyester polyols or polyether polyols of general formula I

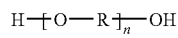

in which R stands for a straight chain alkylene group with 2 to 12 carbon atoms and n is a number between 2 and 20, or completely or partially hydrolyzed polyvinylalcohols of general formula II

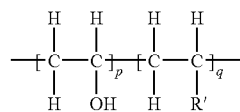

in which R' stands for an alkyl, aryl, or acyl group with 1 to 12 carbon atoms, p and q are numbers between 1 and 20 or with mixtures of these compounds, produced without or in the presence of an alkaline catalyst favoring splitting off of ammonia and the ammonia or the amine liberated was thereby removed from the reaction mixture by means of a stripping gas and/or steam and/or vacuum, is reacted with an alcohol or a phenol with formation of organic carbonates and back formation of the polymeric polyalcohols of formula I or II, which are used in the circuit again for manufacture of a mixture of organic carbonates or carbamates by reaction with urea, substituted ureas, salts or esters of carbamic acid or one of their N-substituted derivatives.

In the method in accordance with the invention for the manufacture of dimethyl carbonate and/or other alkyl carbonates, as alcohols methyl alcohol and/or straight chain or branched aliphatic alcohols having 2 to 10 carbon atoms are employed.

For the manufacture of diphenyl carbonate and/or aryl carbonates phenol and/or substituted phenols are used, which have alkyl groups having 1 to 4 carbon atoms. The reaction in accordance with the invention of the mixture of polymeric alcohols and their carbonates or carbamates with an alcohol or a phenol with formation of organic carbonates is carried out in an advantageous way at temperatures between 10° C. and 270° C. In this connection, processing takes place in the presence of catalysts. For this alkaline reacting salts, oxides, hydroxides, alcoholates of the first and second main group or the 1 to 8 subgroup of the periodic system, basic zeolites or polymeric ion exchangers are suitable as catalysts. For example magnesium or zinc catalysts, which can be employed as oxide or also as acetate can be catalytically effective.

At temperatures between 10° C. and 270° C., a brisk reaction of the mixture of organic carbonates and carbamates takes place with aliphatic or araliphatic alcohols or phenols. The use of a slightly higher pressure of ca. 6 bar and a temperature of about 140 ° C. is advantageous. The equilibrium is established after less than one hour in batch operation.

The back formed polymeric polyalcohols of formula I and II by the processing are fed back into the circuit and once again employed for manufacture of a mixture of organic carbonates or carbamates.

The invention claimed is:

1. A method for the manufacture of an organic carbonate from a mixture of polymeric polyalcohols and their carbonates and carbamates, which through reaction of urea, a substituted urea, a salt or ester of carbamic acid or one of their N-substituted derivatives with a polyalkylkeneglycol, polyesterpolyol or a polyetherpolyol of general formula I

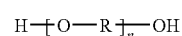

in which R stands for a straight chain or branched alkylene group having 2 to 12 carbon atoms and n is a number between 2 and 20, or having a completely or partially hydrolyzed polyvinylalcohol of general formula II

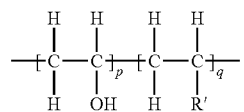

in which R' stands for an alkyl, aryl or acyl group having 1 to 12 carbon atoms, p and q are numbers between 1 and 20, or with mixtures of these compounds, without or in presence of an alkaline catalyst favoring splitting off of ammonia and separation of the ammonia or of the amine liberated thereby is obtainable from the reaction mixture by means of a stripping gas and/or steam and/or vacuum characterized in that this mixture is reacted with alcohols or phenols with formation of their carbonates and back formation of the polymeric polyalcohols of formulas I or II.

2. The method according to claim 1, characterized in that, alkaline reacting salts, oxides, hydroxides, alcoholates with elements of groups Ia, Ib, IIa, IIb, IIIa, IIIb, IVa, IVb, Va, Vb, VIb, VIIb, VIIIb of the Periodic System, basic zeolites, polymeric ion exchangers or tetraalkylammonium salts or triphenylphosphines or tertiary amines are employed as catalysts.

3. The method according to claim 1, characterized in that the back-formed polymeric polyalcohols of formulas I or II are fed back again into the circuit again for the manufacture of a mixture of organic carbonates or carbamates.

4. The method for the manufacture of dimethyl carbonate and/or other organic carbonates according to claim 1, characterized in that methylalcohol, and/or straight chain or branched, aliphatic alcohols having 2-10 carbon atoms are employed.

5. The method for the manufacture of diphenyl carbonate and/or arylcarbonates according to claim 1, characterized in that methylalcohol and/or straight chain or branched aliphatic alcohols having 2 to 10 carbon atoms and/or cyclic alcohols having 5 to 10 carbon atoms or phenol and/or substituted phenols are used, which have alkyl groups having 1 to 4 carbon atoms and/or aromatic alcohols, which have 6 to 20 carbon atoms and/or alcohols containing heteroatoms and/or a mixture of these materials are used.

* * * * *